(12) United States Patent
Tani et al.

(10) Patent No.: US 8,716,424 B2
(45) Date of Patent: May 6, 2014

(54) PROCESS FOR SYNTHESIZING ORGANIC/INORGANIC COMPOSITE

(75) Inventors: Masaaki Tani, Nagoya (JP); Yoshiaki Fukushima, Aichi-gun (JP)

(73) Assignee: Kabushiki Kaisha Toyota Chuo Kenkyusho, Aichi-gun (JP)

( * ) Notice: Subject to any disclaimer, the term of this patent is extended or adjusted under 35 U.S.C. 154(b) by 237 days.

(21) Appl. No.: 12/866,177

(22) PCT Filed: Jan. 28, 2009

(86) PCT No.: PCT/JP2009/051339
§ 371 (c)(1),
(2), (4) Date: Aug. 4, 2010

(87) PCT Pub. No.: WO2009/098978
PCT Pub. Date: Aug. 13, 2009

(65) Prior Publication Data
US 2011/0046403 A1    Feb. 24, 2011

(30) Foreign Application Priority Data
Feb. 5, 2008   (JP) .................................. 2008-025207

(51) Int. Cl.
*C08G 79/10*    (2006.01)
*C08G 77/10*    (2006.01)

(52) U.S. Cl.
CPC ................ *C08G 79/10* (2013.01); *C08G 77/10* (2013.01)
USPC .......................................................... 528/16

(58) Field of Classification Search
CPC .................................. C08G 79/10; C08G 77/10
USPC .......................................................... 528/16
See application file for complete search history.

(56) References Cited

U.S. PATENT DOCUMENTS

| | | | | |
|---|---|---|---|---|
| 5,527,871 | A | * | 6/1996 | Tani et al. ........................ 528/10 |
| 5,756,628 | A | * | 5/1998 | Tani et al. ......................... 528/9 |
| 6,069,220 | A | * | 5/2000 | Hoffmann et al. ............... 528/12 |
| 6,107,505 | A | * | 8/2000 | Yoshida et al. ................ 556/450 |
| 2007/0078277 | A1 | * | 4/2007 | Ackermann ................... 556/470 |

FOREIGN PATENT DOCUMENTS

| | | |
|---|---|---|
| JP | 6 200034 | 7/1994 |
| JP | 8 12899 | 1/1996 |
| JP | 9 241380 | 9/1997 |
| JP | 11 246662 | 9/1999 |
| JP | 11 255898 | 9/1999 |
| JP | 2004 225050 | 8/2004 |
| JP | 2007 100094 | 4/2007 |

OTHER PUBLICATIONS

Taylor, "An introduction to error analysis," 2nd ed. (1997), 329 pages, chs. 1-2 provided.*
Notification of Reasons for Refusal issued Jul. 26, 2012 in Japanese Patent Application No. 2008-025207 with English Translation.
Office Action issued Nov. 13, 2012 in Japanese Application No. 2008-025207 (with English Translation).

* cited by examiner

*Primary Examiner* — Robert Havlin
(74) *Attorney, Agent, or Firm* — Oblon, Spivak, McClelland, Maier & Neustadt, L.L.P.

(57) ABSTRACT

The present invention is characterized in that it is a process for synthesizing an organic/inorganic composite that not only comprises an oxide of silicon and metal, oxide which includes a bond being expressed by "M-O-M" (where "M" independently represents silicon atom or metal atom), but also possesses an organic group which is bonded to a part of silicone atoms at least; and it includes: a preparation step of preparing a raw-material solution by dissolving an organo alkoxysilane, which possesses one or more alkoxy groups and has the silicon atom that is bonded with the organic group by covalent bond, and a metallic compound, which includes the metal atom, in a first solvent, which is a polar solvent; a reaction step of synthesizing the organic/inorganic composite by not only hydrolyzing the organo alkoxysilane and the metallic compound but also condensing them by means of dehydration; and a removal step of adding a second solvent, which does not dissolve compatibly with a solution that has undergone the reaction step, to the solution, thereby dissolving the organic/inorganic composite in the second solvent, and thereafter removing another solution, which does not dissolve compatibly with the second solvent. It is possible to recover the organic/inorganic composite readily by means of the present synthesizing process.

20 Claims, 2 Drawing Sheets

PROCESS FOR SYNTHESIZING ORGANIC/INORGANIC COMPOSITE

CROSS REFERENCE TO RELATED APPLICATION

This application is a 371 of PCT/JP2009/051339, filed on Jan. 28, 2009, and claims priority to Japanese Patent Application No. 2008-025207, filed on Feb. 5, 2008.

TECHNICAL FIELD

The present invention is one which relates to a process for synthesizing organic/inorganic composite that possesses properties of organic material and those of inorganic material combindedly.

BACKGROUND ART

In general, inorganic materials, which are used as major-component materials or fillers for coated films, molded bodies and the like, possess such characteristics as high hardness, heat resistance, and so forth. In the case of using inorganic materials, calcination by means of heating is needed in order to quickly form dense and fine phases from the liquid phases or solutions. Moreover, these inorganic materials are not good in the affinity to organic solvents and organic-matter phases. On the contrary, although organic materials possess such characteristics as flexibility and quick film-forming property at ordinary temperature, they have such disadvantages that they are poorer in the hardness and heat resistance. Consequently, organic/inorganic composites that possess the aforementioned characteristics of inorganic materials and organic materials combinedly, and furthermore in which the aforementioned disadvantages are restricted as much as possible, and processes for producing the same have been investigated heretofore.

For example, in Patent Literature No. 1 and Patent Literature No. 2, lamellar silicone polymers are disclosed, the lamellar silicone polymers having a phyllosillicate-mineral-type lamellar structure that comprises a 2:1-type or 1:1-type laminated body with a tetrahedral sheet in which silicon atom makes the central atom; and an octahedral sheet in which metal makes the central atom, and the lamellar silicone polymers possessing an organic group that bonds with at least apart of the silicon covalently. Moreover, in Patent Literature No. 3, the following are set forth therein: a coated-material composition in which the lamellar silicone polymers set forth in Patent Literature Nos. 1 and 2 are used as fillers; and a process for manufacturing wear-resistant article in which the same is used. A production process for the lamellar silicone polymers set forth in the respective patent literatures will be hereinafter explained in detail.

Figure 1:
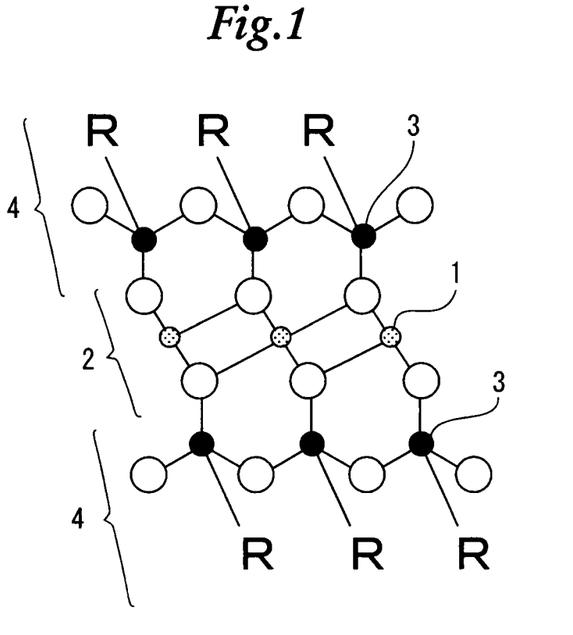
FIG. 1 is an explanatory diagram for illustrating a structure of methacryl magnesium lamellar polymer possessing a phyllosillicate-mineral-type laminated structure that comprises a 2:1-type laminated body.

First of all, a raw-material solution is prepared by adding 3-methacryloxypropyl trimethoxysilane and magnesium chloride hexahydrate to methanol and then stirring them. Next, a sodium hydroxide aqueous solution is added to the raw-material solution while stirring it, and then this mixture solution is turned into gel. Thus, a methacryl Mg lamellar polymer is synthesized, the methacryl Mg lamellar polymer having a phyllosillicate-mineral-type crystalline laminated structure. Note that an outline of the structure of a 2:1-type methacryl Mg lamellar polymer is illustrated in FIG. 1. In the methacryl Mg lamellar polymer, tetrahedral sheets 4, in which silicon atoms 3 (being specified with "●") make the centers, are formed on the opposite sides of an octahedral sheet 2, in which magnesium atoms 1 make the centers. And, as those constituting a part of the tetrahedral sheets 4, organic groups R are bonded to the silicon atoms 3 by means of covalent bond. In the drawing, "○" specifies oxygen atoms.

Thereafter, the methacryl Mg lamellar polymer is isolated in a powdered state by vacuum drying after filtering the gelated mixture solution and then washing it with water.

Patent Literature No. 1: Japanese Unexamined Patent Publication (KOKAI) Gazette No. 6-200,034;
Patent Literature No. 2: Japanese Unexamined Patent Publication (KOKAI) Gazette No. 7-126,396; and
Patent Literature No. 3: Japanese Unexamined Patent Publication (KOKAI) Gazette No. 8-12,899

DISCLOSURE OF THE INVENTION

Assignment to be Solved by the Invention

Since the solution, which has undergone reactions, turns into gel, or since synthesized products precipitate, the resultant synthesized lamellar silicone polymers have been usually separated from the solution, which includes impurities such as sodium chloride, one of the by-products, by filtering the solution as set forth in the aforementioned production process. However, there is a limitation on the size of the lamellar silicone polymers that are separable from the solution by means of filtration. When the lamellar silicone polymers are fine particles, the fine particles might be flushed away along with the solution.

Moreover, as for a drying method after the filtration, evaporating the methanol and water by heating is the most convenient method; however, there is a limitation on the heating temperature because organic parts of the lamellar silicone polymers are weak to heat. Although a drying method using vacuum drying or freeze drying is available, it is hard to say that the method can be a convenient method from the viewpoint of cost and equipment.

In view of the aforementioned problematic issues, it is an object for the present invention to provide a noble synthesizing method that makes it feasible to readily recover organic/inorganic composite like the lamellar silicone polymers.

Means for Solving the Assignment

A process for synthesizing organic/inorganic composite according to the present invention is characterized in that:

it is a process for synthesizing an organic/inorganic composite,
not only the organic/inorganic composite comprising an oxide of silicon and metal, the oxide including a bond being expressed by "M-O-M" (where "M" independently represents silicon atom or metal atom);
but also the organic/inorganic composite possessing an organic group that is bonded to a part of silicone atoms at least; and it includes:
a preparation step of preparing a raw-material solution by dissolving an organo alkoxysilane, which possesses one or more alkoxy groups and has said silicon atom that is bonded with said organic group by covalent bond, and a metallic compound, which includes said metal atom, in a first solvent, which is a polar solvent;
a reaction step of synthesizing said organic/inorganic composite by not only hydrolyzing said organo alkoxysilane and said metallic compound but also condensing them by means of dehydration; and
a removal step of adding a second solvent, which does not dissolve compatibly with a solution that has undergone said reaction step, to the solution, thereby dissolving said organic/inorganic composite in the second solvent, and thereafter removing another solution, which does not dissolve compatibly with the second solvent.

Note that, in the present description, "dissolving" is such a phenomenon that substances (or solutes) dissolve in solvents to turn into uniform mixtures (or solutions), and the following are included: cases where at least apart of solutes turn into ions after dissolving; cases where solutes do not dissociate into ions but exist in the molecular states; molecules and ions associate to be exist; and the like.

Effect of the Invention

The process for synthesizing organic/inorganic composite according to the present invention includes a removal step that becomes a substitute for conventional filtering. In the removal step, an organic/inorganic composite having been synthesized in a reaction step is dissolved in a second solvent that does not dissolve compatibly with a solution that has undergone the reaction step. Although the synthesized organic/inorganic composite dissolves in the second solvent, impurities such as by-products are kept in being dissolved in a polar solvent. And, since the solution that has undergone the reaction step, and the second solvent do not dissolve compatibly with each other but are separated from each other, it is possible to readily remove another solution that includes the impurities, and so the solution that includes the organic/inorganic composite can be recovered. Since the organic/inorganic composite dissolves in the second solvent regardless of its size, such microfine organic/inorganic composites that cannot be taken out by filtering can also remain in the second solvent that has undergone the removal step. As a result, it becomes feasible to recover and then utilize even such microfine organic/inorganic composite that cannot be recovered by filtering. When using microfine organic/inorganic composites as fillers for coated films or molded bodies, the dispersibility is high in raw materials for paint compositions for the coated films, and in raw materials for the molded bodies; moreover, coated films and molded bodes with transparency are obtainable because the smaller the fillers are the less the incident lights are reflected or scattered.

The solution that is obtainable after the removal step is a solution in which the organic/inorganic composite dissolves in the second solvent (hereinafter might be abbreviated to as an "organic/inorganic composite/second-solvent solution" as well). Depending on types of the organic group that the organic/inorganic composite has, it is even feasible to use the "organic/inorganic composite/second-solvent solution" as it is as paint compositions for coated films, or as raw materials for molding molded bodies. Moreover, when using the organic/inorganic composite as fillers for coated films or molded bodies that are made from resins, it is also feasible to use the "organic/inorganic composite/second-solvent solution" that dissolves resins as paint compositions, or as raw materials for molding.

In addition, since many of those second solvents have organic systems, there is such a tendency that the organic/inorganic composite, which exhibits stronger organic properties, is likely dissolve in the second solvents. Consequently, the organic/inorganic composite to be recovered is good in terms of affinity to resins.

In the process for synthesizing organic/inorganic composite according to the present invention, since many of those second solvents to be used at the removal step have organic systems and they exhibit a lower boiling point, it is possible to remove the second solvents without ever exposing the synthesized organic/inorganic composite to high temperatures when isolating the organic/inorganic composite. The isolated organic/inorganic composite, from which the second solvents have been removed, can also be used as fillers by dispersing it in organic solvents or resinous varnishes.

BEST MODE FOR CARRYING OUT THE INVENTION

Hereinafter, a best mode for carrying out a process for producing organic/inorganic composite according to the present invention (might also be abbreviated to as a "synthesizing process according to the present invention" hereinbelow) will be explained.

An organic/inorganic composite to be synthesized in a synthesizing process according to the present invention comprises an oxide of silicon and metal, oxide which includes a bond that is expressed by "M-O-M" (where "M" independently represents silicon atom or metal atom); and it is synthesized via a preparation step, a reaction step and a removal step that will be detailed hereinafter. Explanations will be made on the respective steps hereinbelow.

Preparation Step

The preparation step is a step of preparing a raw-material solution by dissolving an organo alkoxysilane and a metallic compound in a first solvent. Note that the "dissolving" herein also includes such states in which the organo alkoxysilane and/or metallic compound are dispersed as particles in the first solvent.

The organo alkoxysilane possesses one or more alkoxy groups, and has silicon atoms that are bonded with an organic group by covalent bond. The organo alkoxysilane is not limited in particular as far as it can be expressed with a general formula: $R_nSi(OR')_{4-n}$ wherein: n is 1, 2 or 3; R is an organic groups excepting an alkoxy group; and OR' is an alkoxy group. In this instance, Si corresponds to a part of M in an "M-O-M" bond that the present organic/inorganic composite has, and the organic groups correspond to an organic group bonding with a silicon atom that the present organic/inorganic composite has. As for the organo alkoxysilane, being one of organo alkoxysilanes is desirable: acryl-based silanes; vinyl-based silanes; alkylsilanes; aromatic silanes; expoxy-based silanes; amino-based silanes and amines that possess —$NH_2$, —$NHCH_3$ or —$N(CH_3)_2$; ureide-based silanes; halogen-based silanes; mercapto-based silanes; isothiouronium salts; and, in addition to acid anhydrides, organo alkoxysilanes which have nitrogen-containing heterocycles, such as imidazole, imidazoline, pyridine, pyrol, aziridine and triazole; a nitro group (i.e., —NO$_2$); a carbomethoxy group (i.e., —COOCH$_3$); an aldehyde group (i.e., —CH=O); ketone groups (i.e., —(C=O)—R); a hydroxyl group (i.e., —OH); a sulphonyl group (i.e., —S(=O)$_2$—); sulfur-containing heterocycles; a cyano group (i.e., —NC); an isocyanate group (i.e., —N=C=O); and the like.

As for specific examples of the acryl-based silanes, the following can be named: β-acryloxyethyl trimethoxysilane; β-acryloxypropyl trimethoxysilane; γ-acryloxyethyl trimethoxysilane; γ-acryloxypropyl trimethoxysilane; β-acryloxyethyl triethoxysilane; β-acryloxypropyl triethoxysilane; γ-acryloxyethyl triethoxysilane; γ-acryloxypropyl triethoxysilane; β-methacryloxyethyl trimethoxysilane; β-methacryloxypropyl trimethoxysilane; γ-methacryloxyethyl trimethoxysilane; γ-methacryloxypropyl trimethoxysilane; β-methacryloxyethyl triethoxysilane; β-methacryloxypropyl triethoxysilane; γ-methacryloxyethyl triethoxysilane; γ-methacryloxypropyl triethoxysilane; 3-methacryloxypropylmethyl diethoxysilane; and the like. As for specific examples of vinyl-based silanes, the following can be named: vinyl methoxysilane; vinyl triethoxysilane; p-styryl trimethoxysilane; and so forth. As for specific examples of the alkylsilanes, the following can be named: methyltrimethoxysilane; methyltriethoxysilane; ethyltrimethoxysilane; ethyltriethoxysilane; propyltrimethoxysilane; propyltriethoxysilane; hexyltrimethoxysilane; hexyltriethoxysilane; octyltrimethoxysilane; oxyltriethoxysilane; decyltrimethoxysilane; decyltriethoxysilane; dodecyltrimethoxysilane: dodecyltriethoxysilane; tridecyltrimethoxysilane; dodecyltriethoxysilane; hexadecyltrimethoxysilane; hexadecyltriethoxysilane; octadecyltrimethoxysilane; octadecyltriethoxysilane; and so on. As for the aromatic silanes, the following can be named: phenyltrimethoxysilane; phenyltriethoxysilane; etc. As for epoxy-based silanes, the following can be named: 3-glycydoxypropyl trimethoxysilane; 3-glycydoxypropylmethyl diethoxysilane; 3-glycydoxypropyl triethoxysilane; 2-(3,4-epoxycyclohexyl)ethyl trimethoxysilane; and the like. As for the amino-based silanes and amines, the following can be named: 3-aminopropyl triethoxysilane; 3-aminopropyl trimethoxysilane; 3-aminopropyldimethyl ethoxysilane; 3-aminopropylmethyldiethoxysilane; 4-aminobutyltriethoxysilane; 3-aminopropyldiisopropyl ethoxysilane; 1-amino-2-(dimethylethoxysilyl)propane; (aminoethylamino)-3-isobutyldimethyl methoxysilane; N-(2-aminoethyl)-3-aminoisobutylmethyl dimethoxysilane; (aminoethylaminomethyl)phenetyl trimethoxysilane; N-(2-aminoethyl)-3-aminopropylmethyl dimethoxysilane; N-(2-aminoethyl)-3-aminopropyl trimethoxysilane; N-(2-aminoethyl)-3-aminopropyl triethoxysilane; N-(6-aminohexyl) aminomethyl trimethoxysilane; N-(6-aminohexyl) aminomethyl trimethoxysilane; N-(6-aminohexyl) aminopropyl trimethoxysilane; N-(2-aminoethyl)-11-aminoundecyl trimethoxysilane; 11-aminoundecyl triethoxysilane; 3-(m-aminophenoxy)propyl trimethoxysilane; m-aminophenyl trimethoxysilane; p-aminophenyl trimethoxysilane; (3-trimethoxysilylpropyl)diethylenetriamine; N-methylaminopropylmethyl dimehoxysilane; N-methylaminopropyl trimethoxysilane; dimethylaminomethyl ethoxysilane; (N,N-dimethylaminopropyl)trimethoxysilane; (N-acetylglycysil)-3-aminopropyl trimetoxysilane; and so forth. As for the ureide-based silanes, 3-ureidepropyl triethoxysilane, and so on; as for the halogen-based silanes, 3-chloropropyl trimethoxysilane, etc.; as for the mercapto-based silanes, 3-mercaptopropylmethyl dimethosysilane, 3-mercaptopropyl trimethoxysilane, 3-mercaptopropyl triethoxysilane, and the like, can be named. As for isothiouronium salts, N-(trimethoxysilylpropyl)isothiouronium chloride is usable. As for the acid anhydrides, 3-(triethoxysilyl) propyl succinic anhydride, 3-(trimethoxysilyl)propyl succinic anhydride, and so forth, can be named.

Moreover, as for the organo alkoxysilanes having a nitrogen-containing heterocycle, the following can be named: N-(3-triethoxysilylpropyl)-4,5-dihydro imidazole; 2-(trimethoxysilylethyl)pyridine; N-(3-trimethoxysilylpropyl) pyrrole; N-[3-(triethoxysilyl)propyl]-2-carbomethoxy aziridine; and the like. As for the organo alkoxysilanes having a nitro group, the following can be named: 3-(2,4-dinitrophenylamino)propyl ethoxysilane; 3-(triethoxysilylpropyl)-p-nitrobenzamide, and so forth. As for the organo alkoxysilanes having a carbomethoxy group, 2-(carbomethoxy)ethyl trimethoxysilane; as for the organo alkoxysilanes having an aldehyde group, triethoxysilyl butylaldehyde; as for the organo alkoxysilanes having a ketone group, 2-hydroxy-4-(3-methyldiethoxysilylprpoxy)diphenylketone, and so on, can be named. In addition, as for the organo alkoxysilanes having a hydroxyl group, the following can be named: hydroxymethyl triethoxysilane; N-(hydroxyethyl)-N-methylaminopropyl trimethoxysilane; bis(2-hydroxyethyl)-3-aminopropyl triethoxysilane; N-(3-triethoxysilylpropyl)-4-hydroxy butylamide; 11-(triethoxysilyl)undecanol; triethoxysilyl undecanol; ethylene glycol acetal; N-(3-ethoxysilylpropyl)gluconamide; etc. As for the organo alkoxysilanes having a sulfonyl group, (2-triethoxysilylpropoxy)ethoxysulfolane can be named. As for the organo alkoxysilanes having a sulfur-containing heterocycle, 2-(3-trimethoxysilylpropylthio)thiophene can be named. As for the organo alkoxysilanes having a cyano group, 3-cyanopropylphenyl dimethoxysilane, 11-cyanodecyl trimethoxysilane, 3-cyanopropyl trimethoxysilane, 3-cyanopropyl triethoxysilane, and the like; as for the organo alkoxysilanes having an isocyanate group, 3-isocyanatepropyl trimethoxysilane, and so forth, can be named.

It is allowable to use one member of the above-listed organo alkoxysilanes independently, or it is permissible to use two or more of them combinedly.

Moreover, in order to adjust an amount of the organic group that the organic/inorganic composite contains, it is also possible to use one of the aforementioned organo alkoxsilanes with a silicon alkoxide, which does not possess any organic group, combinedly, if needed. As for specific examples of the silicon alkoxide that does not possess any organic group, the following can be named: tetramethoxysilane (or TMOS); tetraethoxysilane (or TEOS); tetra-n-propoxysilane; tetraisopropoxysilane; tetra-n-butoxysilane; tetra-sec-butoxysilane; tetra-tert-butoxysilane; and the like. It is also allowable to use one member of these independently, or it is even permissible to use two or more members of them combindedly. However, when a using amount of the silicon alkoxide is greater, organic/inorganic composites whose inorganic property is stronger are likely to be synthesized. Organic/inorganic composites whose inorganic property is stronger are not desirable as fillers for coated films, or molded bodies being made from resins, because they are poor in the affinity to organic solvents or organic phases. Moreover, when organic/inorganic composites whose inorganic property is stronger are synthesized, a second solvent, which is employed in the removal step that will be detailed later, is limited. Accordingly, there might be cases where organic/inorganic composites whose inorganic property is stronger are not suitable for the synthesizing process according to the present invention. Consequently, when employing a silicon alkoxide, it is desirable to set a proportion of the organo alkoxysilanes at organo alkoxysilane: silicon alkoxide=50:50 or more, or further at 70:30 or more, by ratio of the number of moles with respect to that of the silicon alkoxide.

The metallic compound includes metal atoms corresponding to the balance of "M" in the "M-O-M" bond that the organic/inorganic composite has. The metallic compound can desirably be inorganic salts, organic salts or alkoxides of the metal atoms. Moreover, as for the metal atoms, it is desirable to be at least one member that is selected from the group consisting of magnesium (Mg), aluminum (Al), nickel (Ni), cobalt (Co), copper (Cu), manganese (Mn), iron (Fe), lithium (Li), vanadium (V), zirconium (Zr), and titanium (Ti). That is, as for the metallic compound, the following are employable: chlorides, sulfides, sulfates, nitrates, acetates, methoxides, ethoxides, propoxides, butoxides, and the like, of these metals. It is also allowable to use one member of these independently, or it is even permissible to use two or more members of them combindedly. In addition, when substituting another metal atoms for a part of one of the silicon atoms and metal atoms, it is also allowable to combinedly use a salt or alkoxide that includes those metals.

While making use of an organo alkoxysilane (plus a silicon alkoxide, if needed) and a metallic compound, it is desirable to prepare a raw-material solution so that a molar ratio of the metal atom M' to the silicon atom Si (i.e., M':Si) can be from 1:0.5 to 1:2. In particular, when the organic/inorganic composite is a lamellar organic/inorganic composite that has a phyllosillicate-mineral-type lamellar structure comprising a 2:1-type or 1:1-type laminated body with a tetrahedral structural layer that has a tetrahedral facial structure in which said silicon atom makes the central atom; and an octahedral structural layer that has an octahedral facial structure in which said metal atom makes the central atom, it is possible to selectively produce a 2:1-type or 1:1-type lamellar organic/inorganic composite by means of selecting a value of the ratio, M':Si. For example, when M':Si is such a ratio as from 1:0.5 to 1:1, a 1:1-type lamellar organic/inorganic composite can be synthesized; whereas a 2:1-type lamellar organic/inorganic composite can be synthesized when M':Si is such a ratio as from 3:4 to 1:2.

Moreover, it is also allowable that the organic/inorganic composite can constitute a shell layer involving a core particle that is one organic molecule or an assembled body of organic molecules. In order to obtain such composite particles, it is permissible to prepare a raw-material solution by dissolving titanium alkoxide serving as the metallic compound, an organo alkoxysilane, and organic molecules like ultraviolet-ray absorbing molecules or dye molecules in a first solvent at the preparation step, for instance. Since the organo alkoxysilane coordinates to the titanium alkoxide in the raw-material solution prior to reactions, and furthermore since the titanium alkoxide to which the organo alkoxysilane has coordinated associates around the organic molecules, a shell layer involving core particles can be synthesized after the reactions. When the organic/inorganic composite is composite particles, it is desirable to prepare a raw-material solution so that the M':Si ratio can fall in a range of from 1:0.5 to 1:2, or further in range of from 1:0.8 to 1:1.5.

A first solvent in which an organo alkoxysilane and metallic compound are dissolved is not limited especially as far as being a polar solvent; however, it is allowable that it can comprise one member that is selected from the group consisting of inorganic-system polar solvents and organic-system polar solvents; or it can comprise a mixture solvent of two or more members that are selected from them. To be concrete, the first solvent can be one member that is selected from the group consisting of water that serves as an inorganic polar solvent, alcohols, acetones and organic acids that serve as an organic polar solvent, and inorganic acids, and the like; or it can be a mixture solvent of two or more members that are selected from them; more preferably, the first solvent can be one member that is selected from the group consisting of water, lower alcohols (e.g., chain alcohols whose number of carbon atoms is from 1 to 5), and organic solvents like acetones that are soluble in water; or it can be a mixture solvent of two or more members that are selected from them.

Reaction Step

The reaction step is a step of synthesizing the organic/inorganic composite by not only hydrolyzing the organo alkoxysilane and the metallic compound but also condensing them by means of dehydration. When water exists in the raw-material solution that has been prepared in the preparation step, the organo alkoxysilane and metallic compound undergo not only hydrolysis but also dehydration condensation. Especially, in a case where a metallic inorganic salt and/or metallic organic salt are employed as the metallic compound, it is allowable that the reaction step can include a pH adjustment step of adjusting a pH of the raw-material solution to being alkaline, thereby facilitating the reactions between the organo alkoxysilane and the metallic compound. In the pH adjustment step, it is permissible to add an alkali to the raw-material solution. Types of alkalis to be added are not limited in particular, and it is allowable to add sodium hydroxide, potassium hydroxide, ammonia, or the like, in a form of the aqueous solution. It is permissible that a pH to be adjusted by means of the alkali addition can be a pH at which crystallization occurs at a rate with desired extent or more, and that it cannot be such strong alkaline that the organic group is impaired. Although it cannot be defined unexceptionally because it depends on the types of the organo alkoxysilane and metallic compound, it can be at a pH of from 8 to 10 approximately when synthesizing the lamellar organic/inorganic composite. Due to the existence of water or water and an alkali, the organo alkoxysilane and metallic compound produce -M'-OH in any of the following cases: the metallic compound is first hydrolyzed; or it turns into metallic hydroxide. Since the resulting -M'-OH facilitates the hydrolysis of the organo alkoxysilane and then bonds therewith furthermore, the organic/inorganic composite, which possesses a bond that is expressed with R—Si—O-M', is synthesized. In a case where the lamellar organic/inorganic composite is formed, it is assumed as follows: as the crystalline structure of an octahedral structural layer in which the metal atom M' makes the central atom grows in advance, the silicon of the organo alkoxysilane is bonded to the resultant octahedral structural layer by means of dehydration condensation that occurs after the hydrolysis of the alkoxy group while following the growth; and then the crystalline structure of a tetrahedral structural layer comes to grow up as well while centering around that silicon.

That is, the lamellar organic/inorganic composite comprises a laminated body with a tetrahedral structural layer that is constituted of a tetrahedral facial structure in which the silicon atom makes the central atom; and an octahedral structural layer that is constituted of an octahedral facial structure in which said metal atom makes the central atom. In this instance, at least a part of the silicon atom is bonded with the organic group covalently. As having described already, the lamellar organic/inorganic composite, which comprises a 2:1-type or 1:1-type laminated body that is made of a tetrahedral structural layer and the octahedral structural layer, can be synthesized by adjusting the molar ratio (i.e., M':Si)

between the metallic atom M' and the silicon atom Si in the preparation step. Such a lamellar organic/inorganic composite has a phyllosilicate-mineral-type lamellar structure. Note that the lamellar organic/inorganic composite can be expressed with a general formula, $\{R_n SiO_{(4-n)/2}\}_X[M'O_{z/2}][H_2O]_w$. Note herein that R is said organic group; M' is said metal atom; n is any integer of from 1 to 3; X is an arbitrary number that is not limited to an integer of 0.5 or more and 2 or less; z is a valence number of the metal atom M', and is an integer of 2 or 3; and w is a number of structural water molecules that is not limited to an integer of from $(z/2)-1$ to $(z+1)/2$. The "w" is not limited to an integer, because there are cases where Si—OH bonds are included in the tetrahedral structure.

Moreover, in the reaction step, the reaction of the organo alkoxysilane with the metallic compound occurs even at such a temperature as room temperature approximately; however, it is also allowable to carry it out under such an extent of high-temperature conditions that do not impair the organic group. Depending on conditions, there are cases where the reaction step completes immediately, or there are cases where a certain extent of aging (for a period of from 1 to 2 days approximately, for instance) is required.

Moreover, there are not any limitations especially on the contents of raw materials for the organic/inorganic composite with respect to the raw-material solution as a whole in the reaction step. The contents vary depending on the molecular weights of the organo alkoxysilane and metallic compound (plus a silicon alkoxide, and the like, if needed) that serve as the raw materials for the organic/inorganic composite; however, when trying to prescribe them daringly, it is desirable to set a total amount of raw materials for the organic/inorganic composite to 25% by mass or less when a total mass of the raw-material solution at the reaction step is taken as 100% by mass (note however that, in the case where water or alkalis are added at the reaction step, their amounts are included as well). Being 15% by mass or less is more desirable. In particular, when being 5% by mass or less, microfine organic/inorganic composites with a size of from 10 to 500 nm approximately are synthesized. However, that setting is desirable because the synthesizing process according to the present invention makes it feasible to recover even such microfine organic/inorganic composites that cannot be recovered by filtration.

Removal Step

In the removal step, the organic/inorganic composite is dissolved in a second solvent by adding the second solvent to the solution that has undergone the reaction step. Since the second solvent does not dissolve compatibly with the solution that has undergone the reaction step, the two separate from each other. Thereafter, a solution that does not dissolve compatibly with the second solvent is removed. Note that the solution, which has undergone the reaction step, is an aqueous solution substantially because a great amount of water is usually added at the reaction step. That is, it is allowable that the second solvent can be a solvent that does not dissolve compatibly with water at least but dissolves the organic/inorganic composite therein. In the following explanations, the solution that has undergone the reaction step will be explained as being an "aqueous solution."

Since the aqueous solution that has undergone the reaction step is in gelated states, or in such states that synthesized products have precipitated, it has been filtered out in general to recover the organic/inorganic composites (e.g., colloid particles or precipitated products). On the contrary, in the synthesizing process according to the present invention, the organic/inorganic composite is dissolved selectively by adding the second solvent to the aqueous solution that has undergone the reaction step, without ever carrying out filtration. Since the aqueous solution and second solvent do not dissolve compatibly with each other but separate from each other, it is possible to recover the organic/inorganic composite in such a state as being dissolved in the second solvent.

As for the second solvent, as far as being those which do not dissolve compatibly with the aqueous solution and which can be used as a solvent that can be extracted from the aqueous solution, there are not any limitations on it especially. To be concrete, the following can be named: aliphatic hydrocarbon-system solvents, such as n-pentane, 2-methylbutane, 2,2-dimethylpropane, n-hexane, 2-methylpentane, 3-methylpentane, 2,2-dimethylbutane, 2,3-dimehtylbutane, n-heptane, 2-methylhexane, 3-methylhexane, 2,3-dimethylpentane, 2,4-dimethylpentane, n-octane, 2,2,3-trimethylpentane, 2,2,4-trimethylpentane, n-nonane and n-decane; cycloaliphatic-system solvents, such as cyclopentane, methylcyclopentane, cyclohexane, methylcyclohexane, ethylcyclohexane and cyclooctane; aromatic hydrocarbon-system solvents, such as toluene and xylene; ether-system solvents, such as diethyl ether, diisopropyl ether and dibutyl ether; ester-system solvents, such as triethyl orthoformate, methyl acetate, ethyl acetate and butyl acetate; halogen-system solvents, such as chloroform, carbon tetrachloride, 1,2-dichloroethane, 1,2-dichloroethylene, 1,1,2,2-tetrachloroethane, chlorobenzene, trichloroethylene and tetrachloroethylene; and the like; it is allowable to use one member or two or more members of these. Among them, ethyl acetate, toluene, and chloroform are desirable. Since the organic/inorganic composite have a hydrophilic inorganic portion and a hydrophobic organic portion, it functions like a surface-active agent in solutions; accordingly, it has a tendency to stick onto the boundary face between the aqueous solution and the second solvent and then hinder them from separating from each other. This appears markedly when the second solvent is a completely hydrophobic solvent. The setting is desirable because such a phenomenon can be restrained when employing a second solvent like ethyl acetate that dissolves compatibly with water slightly.

After adding the second solvent to the solution that has undergone the reaction step, they are mixed fully and are then left at rest to make an equilibrium state, and thereby the solution is separated into two layers, an upper layer and a lower layer. Usually, the aqueous solution is put in the lower layer, and a second-solvent solution including the second solution is put in the upper layer. On this occasion, the organic/inorganic composite exists as a solute in the upper layer predominantly. Impurities, for example, like by-products that have been generated at the pH adjustment step, organic/inorganic composites in which inorganic components are included more than necessary, unreacted substances, and so forth, exist as solutes in the lower layer. Note that the aqueous solution is put in the upper layer and a second-solvent solution is put in the lower layer when the second solvent is a heavy solvent like the halogen-system solvents whose specific gravity is heavier than that of water.

And, the organic/inorganic composite/second-solvent solution is recovered by removing the aqueous solution. Depending on the types of organic groups that the organic/inorganic composite possesses, this organic/inorganic composite/second-solvent solution is used as it is for a paint composition or for a raw material for molding, and thereby it is possible to form a coated film or a molded body. When the organic/inorganic composite's organic group possesses a bondable reactive group, which reacts with the other organic/inorganic composite's organic group and is then capable of bonding thereto, at the terminal end, they are bonded with each other by reacting their organic groups with each other, and thereby they make a coated film or molded body. Moreover, it is also allowable to add organic monomers to the organic/inorganic composite/second-solvent solution, or to mix existing paint compositions or molding materials with the organic/inorganic composite/second-solvent solution in order to make it into paint compositions or materials for molding that include fillers.

In addition, at the removal step, it is even permissible to repeatedly carry out the same procedure a plurality of times by altering the types of second solvents, and the like.

It is also allowable that a recovery step of recovering the organic/inorganic composite by removing the second solvent from the organic/inorganic composite/second-solvent solution can be further included after the removal step. The organic/inorganic composite is isolated by experiencing the recovery step. As for a method of removing the second solvent, it is permissible to evaporate the second solvent using an evaporator, and the like. In particular, when the second solvent is one which is selected from the group consisting of ethyl acetate, toluene and chloroform, it is possible to evaporate the second solvent without ever exposing the organic/inorganic composite to high temperatures. It is also allowable to add the organic/inorganic composite, which has been isolated by means of the recovery step, to existing paint compositions or materials for molding that serve as fillers; it is even permissible to use it as paint compositions or molding materials after dispersing it in solvents; furthermore, it is also allowable to add organic monomers to it.

Although the embodiment modes of the synthesizing process for organic/inorganic composite according the present invention have been described so far, the present invention is not limited to the above-described embodiment modes. The present invention can be conducted in various modes to which modifications and improvements are performed, modification and improvements which one of ordinary skill in the art can carry out, within a range not departing from the scope of the present invention.

EXAMPLES

Hereinafter, the present invention will be explained concretely while naming examples of the synthesizing process for organic/inorganic composite according the present invention.

Example No. 1

9.9-g (i.e., 0.05-mol) iron chloride (II) terahydrate was added to 250-mL methanol, and was then stirred therewith. After the iron chloride (II) tetrahydrate had dissolved therein, 24.8-g (i.e., 0.1-mol) 3-methacryloxypropyl trimethoxysilane was added thereto, and was then stirred therewith for 30 minutes, thereby obtaining a raw-material solution.

The thus obtained raw-material solution was stirred along with 1,000-mL ion-exchanged water to mix them using a mixer "MX-151S" for industrial use that was produced by MATSUSHITA ELECTRIC INDUSTRIAL Co., LTD. While keeping stirring them, 1-mol/L sodium hydroxide solution was added thereto in an amount of 100 mL (i.e., NaOH: 0.1 mol), and thereafter were mixed therewith for two minutes.

When the thus mixed solution was transferred to a beaker and was then left at rest therein for one day, brown-colored precipitates were obtained at the lower part in the beaker. A clear supernatant liquid was taken away so as to leave the solution including the precipitates within this beaker in an amount of 500 mL.

Next, 500-mL ethyl acetate was added to the solution that had been left in the beaker, was stirred therewith fully, was transferred to a separating funnel, and was then left at rest therein. Thereafter, the solution inside the separating funnel separated into two layers, an upper layer and a lower layer. The brown-colored precipitates, namely, all of them were dissolved in the ethyl acetate and were then separated into the upper layer. The cock of the separating funnel was opened to flush the lower layer comprising an aqueous solution out from the bottom, and then a brown-colored solution (i.e., the upper layer) was taken out from the top of the separating funnel.

Upon removing the ethyl acetate completely by condensing the thus taken-out upper-layer solution with a rotary evaporator (bath temperature: 30° C.), a brown-colored methacryl iron lamellar composite was obtained in an amount of 52.2 g.

Example No. 2

12.1-g (i.e., 0.05-mol) aluminum chloride (III) hexahydrate was added to 250-mL methanol, and was then stirred therewith. After the aluminum chloride (III) hexahydrate had dissolved therein, 24.8-g (i.e., 0.1-mol) 3-methacryloxypropyl trimethoxysilane was added thereto, and was then stirred therewith for 30 minutes, thereby obtaining a raw-material solution.

The thus obtained raw-material solution was stirred along with 1,000-mL ion-exchanged water to mix them using the aforementioned industrial-use mixer. While keeping stirring them, 1-mol/L sodium hydroxide solution was added thereto in an amount of 150 mL (i.e., NaOH: 0.15 mol), and thereafter were mixed therewith for one minute.

When the thus mixed solution was transferred to a beaker and was then left at rest therein for one day, white-colored precipitates were obtained at the lower part in the beaker. A clear supernatant liquid was taken away so as to leave the solution including the precipitates within this beaker in an amount of 100 mL.

Next, 100-mL ethyl acetate was added to the solution that had been left in the beaker, was stirred therewith fully, was transferred to a separating funnel, and was then left at rest therein. Thereafter, the solution inside the separating funnel separated into two layers, an upper layer and a lower layer. The white-colored precipitates, namely, all of them were dissolved in the ethyl acetate and were then separated into the upper layer. After opening the cock of the separating funnel to flush the lower layer comprising an aqueous solution out from the bottom, a 30-mL saturated sodium chloride aqueous solution to the remaining solution (i.e., the upper layer), and was then mixed therewith. When leaving them at rest for a while, they separated into two layers, an upper layer and a lower layer, both of which were transparent. The cock of the separating funnel was opened again to flush the lower layer comprising a sodium chloride aqueous solution out from the bottom, and then the upper layer was taken out from the top of the separating funnel.

Upon removing the ethyl acetate completely by condensing the thus taken-out upper-layer solution with a rotary evaporator (bath temperature: 30° C.), a transparent methacryl Al lamellar composite was obtained in an amount of 14.7 g.

The isolated methacryl Al lamellar composite dissolved in 1-methoxy-2-propanol completely, and then turned into a transparent solution. This transparent solution was applied onto one of the opposite surfaces of a glass substrate and was then dried, and thereby a transparent coated film comprising the methacryl Al lamellar composite was obtained.

Figure 2:
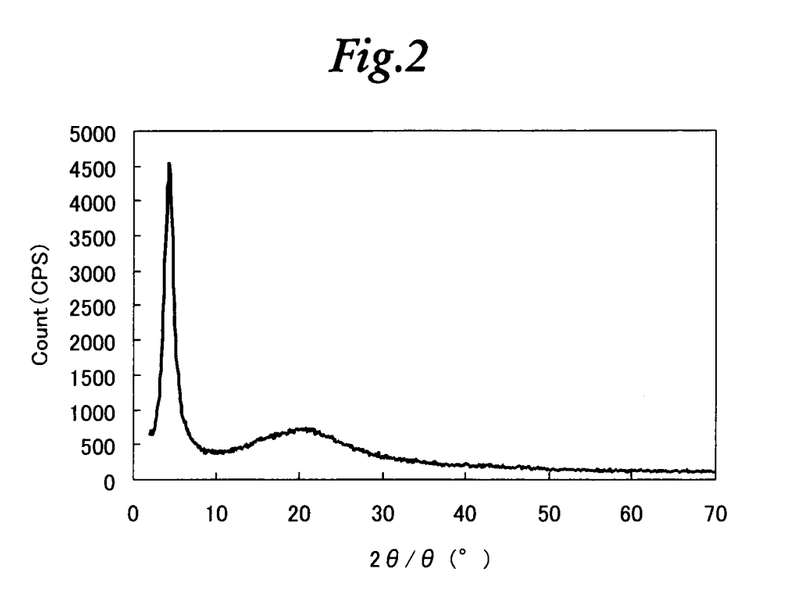
FIG. 2 illustrates an X-ray diffraction pattern of a methacryl aluminum lamellar composite that was obtained by means of a process for synthesizing organic/inorganic composite according to the present invention.

Next, an X-ray diffraction (or XRD) measurement of this transparent coated film was carried out. For the XRD measurement, an X-ray diffraction apparatus "RINT2200" produced by RIGAKU Co., Ltd. was used, the measurement was conducted from 2 and up to 70° by means of the CuKα ray (acceleration voltage: 40 kV, and current: 30 mA). The thus obtained diffraction pattern is illustrated in FIG. 2. A diffraction peak that indicates a spacing of lattice planes in a lamellar structure was observed at 4.3°. A distance between layers that was calculated from this diffraction peak was 20.5 Å (i.e., 2.05 nm).

Figure 3:
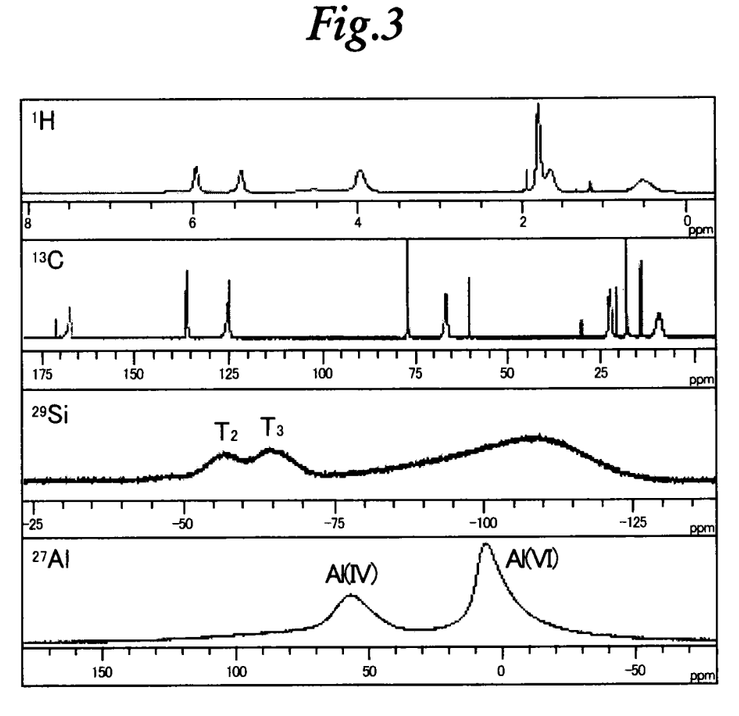
FIG. 3 illustrates nuclear magnetic resonance (or NMR) spectra of a methacryl aluminum lamellar composite that was obtained by means of a process for synthesizing organic/inorganic composite according to the present invention.

In addition, the isolated methacryl Al lamellar composite was further dissolved in deuterochloroform, and a nuclear magnetic resonance (or NMR) spectrum was measured for each of nuclear species, hydrogen ($^1$H), carbon ($^{13}$C), silicon ($^{29}$Si) and aluminum ($^{27}$Al). The thus measured results are illustrated in FIG. 3. It was ascertained from the spectra of $^1$H and $^{13}$C that an organic structure (i.e., the methacryl group), which the organo alkoxysilane possessed, was present as it was. It was ascertained from the spectrum of $^{29}$Si that the hydrolysis and dehydration condensation developed fully to be completed. Moreover, it was ascertained from the spectrum of $^{27}$Al that the aluminum was taken in into the composite, and that its state turned into being substantially the same as that of smectite, one of representative lamellar silicates that contain aluminum.

Example No. 3

122.5-g (i.e., 0.05-mol) copper sulfate (II) pentahydrate was added to 250-mL methanol. After the copper sulfate was dispersed in the methanol, 24.8-g (i.e., 0.1-mol) 3-methacryloxypropyl trimethoxysilane was added thereto, and was then stirred therewith for 30 minutes, thereby obtaining a raw-material solution.

Upon stirring the thus obtained raw-material solution along with 1,000-mL ion-exchanged water to mix them using the aforementioned industrial-use mixer, blue-colored transparent solution was obtained. Upon adding 1-mol/L sodium hydroxide solution thereto in an amount of 100 mL (i.e., NaOH: 0.1 mol) while keeping stirring this solution; and mixing them thereafter for two minutes, blue-colored products engulfed the air and then surfaced.

The thus mixed solution was transferred to a beaker to leave it at rest therein for one day, and then the solution including the products was ladled out. 500-mL ethyl acetate was added to the resultant ladled-out solution, was stirred therewith fully, was transferred to a separating funnel, and was then left at rest therein. Thereafter, the solution inside the separating funnel separated into two layers, an upper layer and a lower layer. The blue-colored products, namely, all of them were dissolved in the ethyl acetate and were then separated into the upper layer. The cock of the separating funnel was opened to flush the lower layer comprising an aqueous solution out from the bottom, and then a blue-colored solution (i.e., the upper layer) was taken out from the top of the separating funnel.

Upon removing the ethyl acetate completely by condensing the taken-out upper-layer solution with a rotary evaporator (bath temperature: 30° C.), a rubber-like and blue-colored methacryl copper lamellar composite was obtained in an amount of 23.6 g.

The isolated methacryl copper lamellar composite dissolved in 1-methoxy-2-propanol completely, and then turned into a transparent solution. This transparent solution was applied onto one of the opposite surfaces of a glass substrate and was then dried, and thereby a bluish transparent coated film was obtained.

Figure 4:
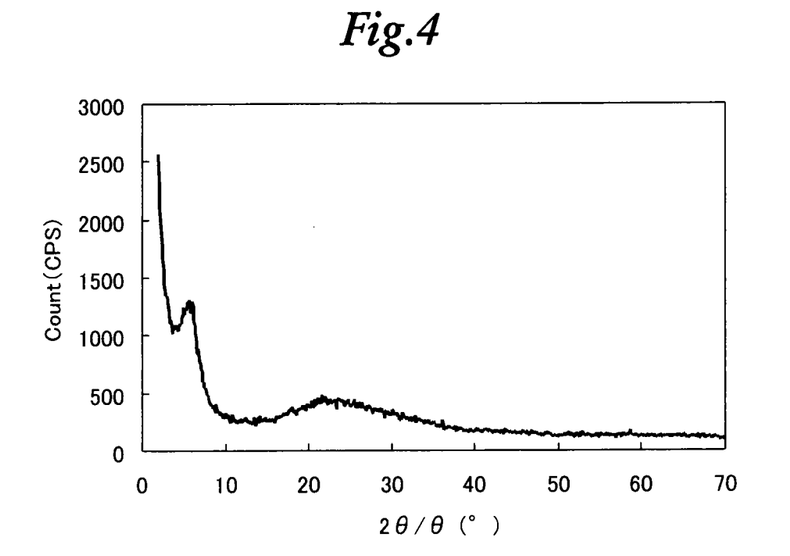
FIG. 4 illustrates an X-ray diffraction pattern of a methacryl copper lamellar composite that was obtained by means of a process for synthesizing organic/inorganic composite according to the present invention.

Next, an X-ray diffraction (or XRD) measurement of this transparent coated film was carried out in the same procedure as set forth above. The resulting diffraction pattern is illustrated in FIG. 4. A diffraction peak that indicates a spacing of lattice planes in another lamellar structure was observed at 5.7°. A distance between layers that was calculated from this diffraction peak was 15.5 Å (i.e., 1.55 nm).

Example No. 4

51.1-g (i.e., 0.25-mol) magnesium chloride hexahydrate was added to 500-mL methanol, and was then stirred therewith. After the magnesium chloride hexahydrate had dissolved therein, 118-g (i.e., 0.5-mol) 3-glycydoxypropyl trimethoxysilane ("SILA-ACE S510" produced by CHISSO CORPORATION) was added thereto, and was then stirred therewith, thereby obtaining a raw-material solution.

After leaving the thus obtained raw-material solution as it was for one night, a 1-mol/L sodium hydroxide solution in which 20-g (i.e., 0.5 mol) sodium-hydroxide pellets were dissolved in 500-mL ion-exchanged water was added thereto, and was mixed therewith for thirty minutes.

After transferring the thus mixed solution to a beaker and then leaving it at rest therein for one day, 3,000-mL chloroform was added thereto, and was then stirred therewith for 1 hour. When transferring this solution to a separating funnel and then leaving it at rest therein for one day, the solution inside the separating funnel separated into two layers, an upper layer and a lower layer. The lower layer comprising an aqueous solution was flushed out from the bottom of the separating funnel by opening the cock, and then an epoxy-based magnesium lamellar composite/chloroform solution (i.e., the upper layer) was taken out from the top of the separating funnel.

After a solid-content concentration of the thus obtained epoxy-based Mg lamellar composite/chloroform solution was measured, an epoxy resin ("EPICOAT 604" produced by JAPAN EPDXY RESIN Co., Ltd.) was added to it to dissolve it therein. A compounding amount of the epoxy resin was set at the following three kinds: a mass ratio of the epoxy-based Mg lamellar composite to the epoxy resin, i.e., the epoxy-based Mg lamellar composite:the epoxy resin=1:2, 2:10, and 1:10. Next, the chloroform was evaporated from each of the solutions with a rotary evaporator (bath temperature: 40° C.), and then the deaeration was carried out while heating each of them in a 60-° C. oil bath, thereby obtaining epoxy-based Mg lamellar composite/epoxy resin mixtures. Any one of the mixtures was transparent. In other words, the epoxy-based Mg lamellar composites that were obtained by means of the process according to the present example were microfine, and were abundant in terms of the dispersibility to organic solvent.

Comparative Example No. 1

After preparing the raw-material solution following the same procedure as that of Example No. 4, a sodium hydroxide solution was added thereto, was stirred therewith, and was then mixed therewith following the same procedure as that of Example No. 4.

After leaving the thus mixed solution at rest for one day, the filtration was carried out, and then recovered substances were washed with water. The recovered substances, which had been washed with water, were mixed along with 2-L ion-exchanged water using the aforementioned mixer for industrial use, thereby obtaining a liquid suspension in which the recovered substances were dispersed. This liquid suspension was freeze dried in vacuum, thereby obtaining a powder of an epoxy-based Mg lamellar composite.

The thus obtained powder and an epoxy resin ("EPICOAT 604" produced by JAPAN EPDXY RESIN Co., Ltd.) were kneaded with each other by means of an automatic mortar "ANM200W" that was produced by NITTO KAGAKU Co., Ltd. In this instance, a compounding amount of the epoxy resin was set at the following three kinds: a mass ratio of the epoxy-based Mg lamellar composite to the epoxy resin, i.e., the epoxy-based Mg lamellar composite: the epoxy resin=1:2, 2:10, and 1:10. After kneading them for 30 minutes, white-colored and opaque epoxy-based Mg lamellar composite/epoxy resin mixtures were obtained. In other words, in the epoxy-based Mg lamellar composites that were obtained by means of the process according to the present comparative example, composites whose particulate size was larger, and composite whose dispersibility into the organic solvent was lower were included.

Note that, when these mixtures that had been obtained following the aforementioned procedure were collected in a small amount and were then pressed and elongated between two pieces of glass-slide plates, undispersed epoxy-based Mg lamellar composites could be confirmed in a large quantity.

EXPLANATION ON REFERENCE NUMERALS

1: Magnesium Atom;
2: Octahedral Sheet;
3: Silicon Atom;
4: Tetrahedral Sheet

The invention claimed is:

1. A process for synthesizing an organic/inorganic composite, comprising:
dissolving i) a metallic compound comprising a metal atom and ii) an organo alkoxysilane comprising at least one alkoxy group and a silicon atom that is covalently bonded to an organic group in a first solvent, which is a polar solvent, thereby preparing a raw material solution;
synthesizing by hydrolyzing and condensing said organo alkoxysilane and said metallic compound present in said raw material solution to obtain a synthesized organic/inorganic composite present in said raw material solution;
adding a second solvent, which does not dissolve compatibly with said raw material solution that has undergone said hydrolyzing and condensing, to the raw material solution, thereby dissolving said synthesized organic/inorganic composite in the second solvent to form a second solution;
equilibrating the second solution to form a first aqueous layer and a second layer comprising the synthesized organic/inorganic composite, said first aqueous layer and said second layer being separate layers;
and thereafter removing the aqueous layer to separate the second layer from the aqueous layer to obtain a third solution comprising the synthesized organic/inorganic composite,
wherein
the synthesized organic/inorganic composite comprises an oxide of silicon and metal and an organic group that is bonded to the silicon atom;
the oxide comprises a bond expressed by formula (I)

$$M-O-M \qquad (1),$$

where M independently represents a silicon atom or a metal atom;
the synthesized organic/inorganic composite having a phyllosillicate-mineral lamellar structure comprising a 2:1 or 1:1 laminated body with a tetrahedral structural layer that is constituted of a tetrahedral facial structure in which said silicon atom makes the central atom; and
an octahedral structural layer that is constituted of an octahedral facial structure in which said metal atom makes the central atom.

2. The process according to claim 1, wherein:
said synthesizing comprises adding water to said raw-material solution; and
the process further comprises removing an aqueous solution, which has undergone said synthesizing, after adding said second solvent, which does not dissolve compatibly with water at least, to the aqueous solution.

3. The process according to claim 1, wherein said first solvent is at least one member selected from the group consisting of an inorganic-system polar solvent, and an organic-system polar solvent.

4. The process according to claim 3, wherein said first solvent is at least one member selected from the group consisting of water, a lower alcohol, and acetone.

5. The process according to claim 1, wherein said second solvent is one or more members that are selected from the group consisting of ethyl acetate, toluene and chloroform.

6. The process according to claim 1, wherein said synthesizing further comprises adjusting a pH of said raw-material solution to being alkaline, thereby facilitating a reaction between said organo alkoxysilane and said metallic compound.

7. The process according to claim 1 further comprising recovering said organic/inorganic compound by removing said second solvent after said removal.

8. The process according to claim 1, wherein said metal atom is at least one member selected from the group consisting of magnesium (Mg), aluminum (Al), nickel (Ni), cobalt (Co), copper (Cu), manganese (Mn), iron (Fe), lithium (Li), vanadium (V), zirconium (Zr), and titanium (Ti).

9. The process according to claim 1, wherein said metallic compound is an inorganic salt, organic salt or alkoxide of said metal atom.

10. The process according to claim 1, wherein said lamellar organic/inorganic composite is expressed by a general formula:

$$\{R_nSiO_{(4-n)/2}\}X[M'O_{z/2}][H_2O]_w \text{ wherein:}$$

R is said organic group;
M' is said metal atom;
n is any integer of from 1 to 3;
X is an arbitrary number that is not limited to an integer of 0.5 or more and 2 or less;
z is a valence number of the metal atom M', and is an integer of 2 or 3; and w is a number of structural water molecules that is not limited to an integer of from $(z/2)-1$ to $(z+1)/2$.

11. The process according to claim 1, wherein a raw material for said synthesized organic/inorganic composite comprises said organo alkoxysilane and said metallic compound, which are present in an amount of 5% by mass or less in said synthesizing when a total mass of said raw-material solution at the synthesizing is taken as 100% by mass.

12. The process according to claim 1, wherein said first solvent is a mixture consisting of water and an organic-system polar solvent soluble in said water.

13. The process according to claim 1, wherein said synthesizing comprises precipitating or gelating said synthesized organic/inorganic composite in the solution of said synthesizing, and the process further comprises:
   removing a portion of said raw material solution that does not contain said synthesized organic/inorganic composite prior to said removing.

14. The process according to claim 1, wherein said second solvent consists of ethyl acetate.

15. The process according to claim 1, wherein said second solvent consists of a mixture of ethyl acetate and at least one of toluene and chloroform.

16. The process according to claim 1, wherein said second solvent consists of a mixture of ethyl acetate and toluene.

17. The process according to claim 1, wherein said second solvent consists of a mixture of ethyl acetate and chloroform.

18. The process according to claim 1, wherein said second solvent consists of a mixture of ethyl acetate, toluene, and chloroform.

19. The process according to claim 1, wherein a raw material for said synthesized organic/inorganic composite comprises said organoalkoxysilane and said metallic compound, which are present in an amount of 5% by mass or less in said synthesizing when a total mass of said raw-material solution at the synthesizing is taken as 100% by mass, and
   microfine organic/inorganic composites having a size of from 10 to approximately 500 nm are present in the raw material solution after said synthesizing has been carried out.

20. The process according to claim 1, wherein a raw material for said synthesized organic/inorganic composite comprises said organoalkoxysilane and said metallic compound, which are present in an amount of 15% by mass or less in said synthesizing when a total mass of said raw-material solution at the synthesizing is taken as 100% by mass.

* * * * *